United States Patent [19] [11] 4,208,372
Huber [45] Jun. 17, 1980

[54] APPARATUS FOR GENERATING AND TRANSFERRING A GASEOUS TEST SAMPLE TO AN ATOMIC ABSORPTION SPECTROMETER

[75] Inventor: Bernhard W. Huber, Uberlingen, Fed. Rep. of Germany

[73] Assignee: Bodenseewerk Perkin-Elmer & Co., GmbH, Uberlingen, Fed. Rep. of Germany

[21] Appl. No.: 896,541

[22] Filed: Apr. 14, 1978

[30] Foreign Application Priority Data

Apr. 26, 1977 [DE] Fed. Rep. of Germany ....... 2718381
Aug. 5, 1977 [DE] Fed. Rep. of Germany ....... 2735281
Oct. 29, 1977 [DE] Fed. Rep. of Germany ....... 2748685

[51] Int. Cl.$^2$ ............................................. G01N 27/66
[52] U.S. Cl. ........................................ 422/65; 422/68; 422/81
[58] Field of Search ............. 23/259, 253 R; 222/373; 422/68–79, 81, 65

[56] References Cited

U.S. PATENT DOCUMENTS

| 3,190,731 | 6/1965 | Weiskopf | 23/259 X |
| 3,536,450 | 10/1970 | Dus et al. | 23/259 X |
| 3,698,870 | 10/1972 | DeJong | 23/259 X |
| 3,801,282 | 4/1974 | Manning et al. | 23/259 X |
| 3,844,719 | 10/1974 | Hammitt | 23/253 R |
| 3,929,411 | 12/1975 | Takano | 23/259 X |
| 3,933,436 | 1/1976 | Naono | 23/259 X |
| 3,963,420 | 6/1976 | Matsumoto et al. | 23/259 X |
| 4,002,269 | 1/1977 | Negersmith | 23/259 X |
| 4,025,311 | 5/1977 | Bochinski | 23/253 R |
| 4,083,690 | 4/1978 | Inoue | 23/259 X |

OTHER PUBLICATIONS

Beckman 'Instruments' Inc. Bulletin, M-2029, Jul. 1975.

Primary Examiner—Michael S. Marcus
Attorney, Agent, or Firm—S. A. Giarratana; F. L. Masselle; E. T. Grimes

[57] ABSTRACT

Atomic absorption spectrometer sample supply apparatus for producing a gaseous sample for analysis and for transferring the sample to the atomic measuring cuvette. The sample supply is in a sealed vessel and, by directing the flow of a pressurized inert gas, the sealed sample vessel is first purged of contaminating air, a volatilizing reagent is forced by inert gas pressure into the sample, and a small specimen of the gaseous sample is transferred by gas pressure into the cuvette inlet tube.

10 Claims, 5 Drawing Figures

APPARATUS FOR GENERATING AND TRANSFERRING A GASEOUS TEST SAMPLE TO AN ATOMIC ABSORPTION SPECTROMETER

CROSS-REFERENCE TO RELATED APPLICATION

The invention described and claimed herein is an improvement over that described and claimed in copending application Ser. No. 835,070, filed Sept. 21, 1977 now U.S. Pat. No. 4,138,215. The invention described in this copending application performs the same function as the present invention but in a more complex and costly arrangement requiring a reagent pump, a gas circulating pump, a magnetic stirrer, solenoid gas valves, and a complex control device that selectively energizes the pump's stirrer and valves to first flush the sample vessel of contaminated air followed by pumping the reagent into the sample vessel, mixing it, and then transporting the gaseous sample by inert gas pressure.

The invention described in the copending application was a substantial advance over the then existing prior art in which all valves, pumps, and mixers were manually controlled as described in Bulletin M-2029, by Beckman Instrument Company. While the invention described in the copending application performs very satisfactorily, its complexity renders it costly and unsuitable for commercial application.

The present invention eliminates the reagent and recirculating pumps, the magnetic stirrer and the complex timing control, thereby greatly simplifying the apparatus and making it quite suitable for high-volume and high-quality spectrophotometric analyses.

BRIEF DESCRIPTION OF THE INVENTION

Briefly described, the apparatus of the invention includes a closed sample vessel, a closed reagent vessel, a source of inert gas, and an automatic valve arrangement in the conduit circuit between the gas source and the vessels. In a first mode, the valve arrangement passes a large gas flow through the sample vessel to flush contaminating air from the vessel and associated conduits. In its second mode, the valve arrangement applies gas pressure to force reagent from its closed vessel into the sample vessel while simultaneously admitting a small separate gas flow into the sample vessel for forcing small quantities of the gaseous sample into the spectrometer cuvette conduit. Intermixing of the reagent with the sample is accomplished without possibility of siphoning between vessels by a structure that admits the reagent into the bottom of the sample vessel. The novel apparatus of the invention is particularly adaptable for automatic analyses of samples contained in the vessels carried by a turntable and consecutively moved into an operating position where the contained sample is volatilized and a portion extracted for absorption analysis.

DESCRIPTION OF THE DRAWINGS

In the drawings illustrating preferred embodiments of the invention.

DETAILED DESCRIPTION

Figure 1:
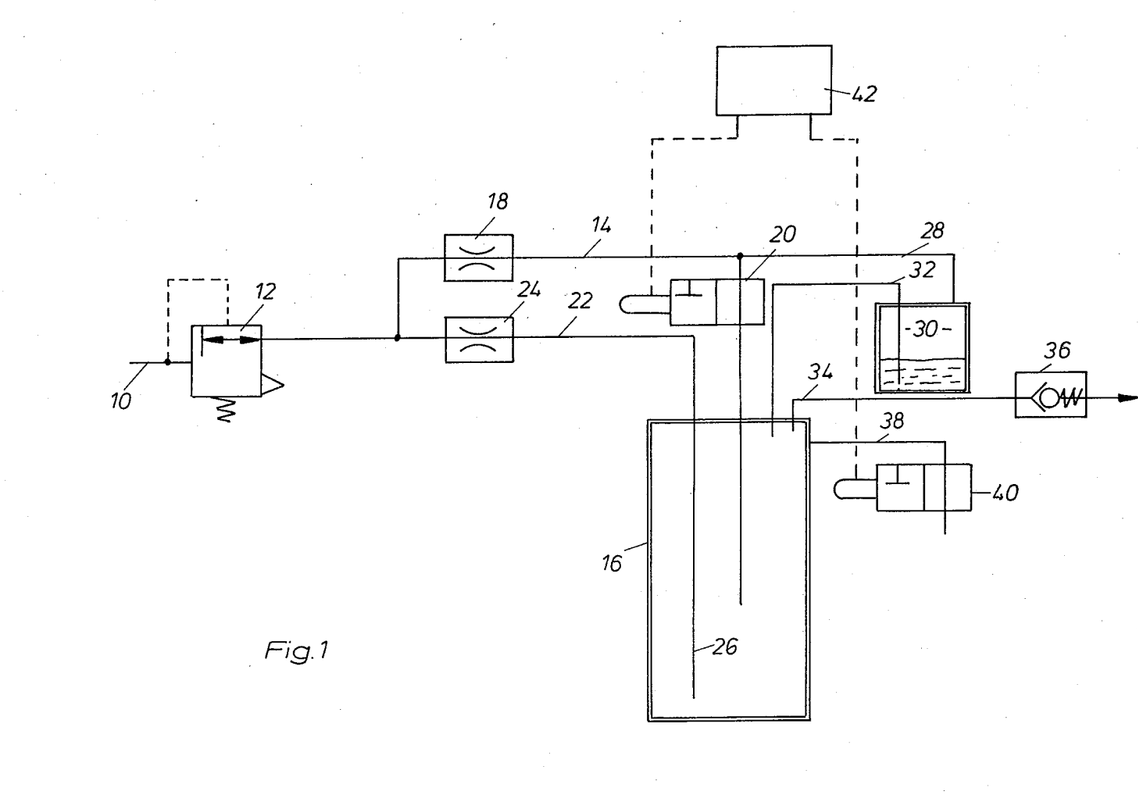
FIG. 1 is a schematic circuit diagram illustrating the various components of the apparatus of the invention.

Turning now to the circuit diagram of FIG. 1, the reference numeral 10 designates the inlet from a source of inert gas, such as argon. Gas inlet 10 is connected to a suitable pressure regulator 12, the output of which is branched into a first conduit 14 and a second conduit 22. The conduit 14 contains an adjustable restrictor 18 which permits a relatively large flow of inert gas to flow through the conduit 14 and through a solenoid controlled shutoff valve 20 into a sealed sample vessel 16. The second conduit 22 from the pressure regulator 12 is directed through a second adjustable restrictor 24 which limits the gas flow to relatively small quantity and which passes into tube 26 within the sample vessel 16. Tube 26 extends nearly to the bottom of the vessel 16 so that the inert gas flowing from the end of tube 26 will bubble through the sample contained within the vessel 16.

Before entering the shutoff valve 20, the gas inlet conduit 14 is branched into a connecting conduit 28 which enters a sealed reagent vessel 30 containing, for example, a reagent, such as $NaBH_4$. A reagent dispensing tube 32 extends from the bottom of the supply vessel 30 and into the sealed sample vessel 16. While all conduits or tubes heretofore described may be any suitable size, the dispensing conduit 32 is preferably a small diameter tubing or capillary, or may have a small flow-restricting section so that, upon the application of inert gas pressure through conduit 28 into the vessel 30, a controlled flow of the liquid reagent will pass into the sample vessel 16.

An outlet conduit 34 leads from the sample vessel 16 and through a suitable check valve 36 to the intake conduit of the atomizing cuvette of the absorption spectrometer. A second outlet conduit 38 extends from the sample vessel 16 and through a solenoid shutoff valve 40 into the atmosphere. The solenoid control valves 20 and 40 are operated simultaneously by a solenoid valve control unit 42.

In operation, shutoff valves 20 and 40 are initially opened so that the large flow of inert gas will flow through the conduit 14 and through valve 20 into the sample vessel 16. Since valve 40 is also open, the inert gas will displace any air or other contaminating gases which will be vented through the valve 40. After contaminants have been purged from the system, the control unit 42 closes the valves 20 and 40 so that the pressure within the conduit 14 is now applied to the sealed reagent vessel 30 to force a controlled quantity of the reagent through the dispensing tube 32 into the vessel 16. Simultaneously, the small flow of gas through conduit 22 and bubbling from the end of the tube 26 will create a pressure within the vessel 16 that will transport a sample, now in a gaseous form by reaction with the reagent, through the outlet conduit 34 and check valve 36 to the atomizing cuvette. After a suitable time necessary to complete the spectrometer analysis, control unit 42 again opens the valves 20 and 40, thereby releasing the pressure within the reagent vessel 30 to stop the flow of reagent through the dispensing tube 32 while simultaneously starting to flush the sample vessel 16.

It will be appreciated that the apparatus schematically illustrated in FIG. 1 is presented to describe the various components and the associated process. It is apparent that the apparatus as illustrated would permit a continuous flow of the reagent from its vessel 30 into the sample vessel 16 by siphon action. Furthermore, no provision has been described for intermixing the reagent with the sample, a step heretofore provided by a magnetically coupled stirrer adjacent the floor of the sample vessel. It has been discovered that mixing, such as by a magnetic stirrer, is not necessary if the reagent is admitted through a dispensing tube that ends near the bottom of the sample vessel so that the reagent may bubble through the contained sample. While an intimate mixture is obtained without an external stirrer in such a configuration, the problem of siphoning between the reagent vessel and the sample vessel is further complicated and would appear to require the addition of a third solenoid controlled valve to the dispensing conduit. This is not necessary in the embodiments to be hereinafter described.

Figure 2:
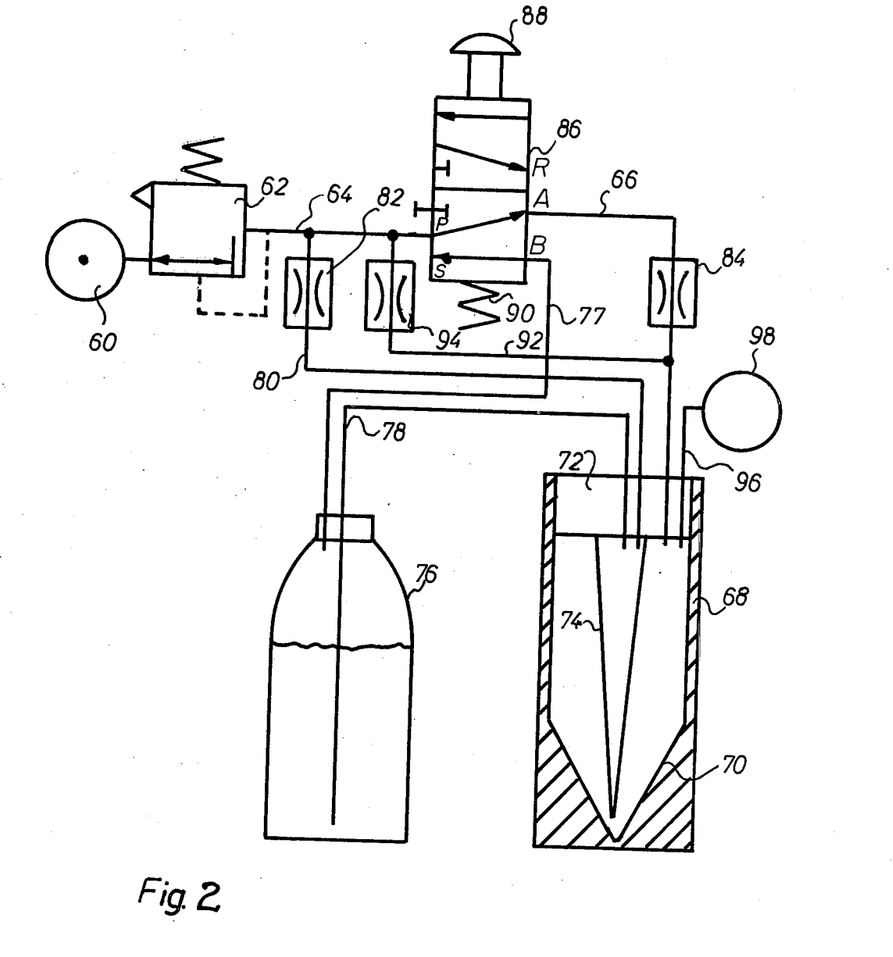
FIG. 2 is a schematic diagram illustrating the details of the apparatus of the invention using a manually controlled directional valve.

FIG. 2 is a schematic diagram illustrating apparatus similar to that described in connection with FIG. 1 but with a novel sample vessel in which the reagent is admitted near the bottom without danger of cross-siphoning between reagent and sample vessels. An inert gas from source 60 is applied through a suitable reducing regulator 62 to the gas inlet conduit 64 where it passes through a valve 86, to be subsequently described, and through the gas inlet conduit 66 into the closed sample vessel 68. Sample vessel 68 has a conical bottom 70 and its top is sealed with a sealing plug 72. The sealing plug 72 supports a hollow funnel-shaped insert 74 which is centrally located on the bottom of the plug 72 and which has a small opening near the conical bottom 70 of the vessel 68. A sealed reagent supply vessel 76 receives an inert air pressure through conduit 77 and contains a dispensing conduit 78 that extends from the bottom of the supply vessel 76 and through the sealing plug 72 into the interior portion of the funnel insert 74 in vessel 68. A gas conduit 80, which contains a flow restrictor 82 but which is otherwise permanently open, also passes through the sealing plug 72 into the interior of the funnel insert 74 so that the reagent entering the core of the funnel insert 74 will be forced from the open tip into the sample, where they will become thoroughly mixed without the necessity of providing additional stirring means.

A flow restrictor 84 is inserted in the gas inlet conduit 66 to permit a relatively large flow of gas through conduit 66 into the sample vessel 68. In addition, a flow restrictor 94, connected between gas inlet 64 and the supply vessel 68, permits a continuous small flow of inert gas into the vessel, as does the restrictor 82.

Valve 86 is a five-port, two-direction control valve and is inserted between the gas inlet conduit 64 and the conduit 66 and is manually operated by a pushbutton 88. The valve 86 is illustrated in FIG. 2 in its inoperative position normally maintained by the bias spring 90. Valve 86 contains five ports arbitrarily designated as R, P, S, A, and B. In the illustrated inoperative position, gas inlet conduit 64 is connected to the port P and conduit 66 is connected to port A so that inert gas will flow from conduit 64 to conduit 66. In the illustrated inoperative position, the port R is closed, the port S vents into the atmosphere, and the port B is connected to the conduit 77 so that an atmospheric pressure will exist within the closed reagent supply vessel 76.

In its operative position, the upper portion of the illustrated control valve 86 is in the circuit so that the conduit 66 connected to port A is sealed off at port R, and the connecting conduit 77 connected to port B is now connected through the valve 86 to the port P and the gas inlet conduit 64.

In operation, valve 86 is initially in its illustrated inoperative position so that gas from the source 60 passes through the conduit 64, conduit 66 and large flow restrictor 84 into the sample vessel 68 and out through the outlet conduit 96 to flush contaminating gases from the vessel 68 and its associated conduits. Since the gas inlet conduit 77 of the reagent vessel 76 is connected through the valve 68 to the atmosphere, there is no pressure within the vessel 76 and no reagent will flow through the dispensing conduit 78 into the sample vessel 68. Because the pressure within the vessel 68 and insert 74 is slightly higher than the atmospheric pressure in the reagent vessel 76, there is no siphoning of the reagent from the vessel 76 into the sample vessel 68. And since the end of dispensing tube 78 is not terminated in the sample, there cannot be any reverse siphoning from the sample vessel into the reagent vessel 76.

When it is desired to make a spectrometer analysis of the sample in vessel 68, the pushbutton 88 of the valve 86 is actuated so that the large flow gas conduit 66 is sealed at the port R of the valve 86 and the connecting conduit 77 is connected to the input port P and the gas inlet conduit 64. The inert gas in the conduit 64 is then applied through connecting conduit 77 and into the reagent vessel 76 to force a supply of reagent through the small dispensing conduit 78 into the center of the funnel insert 74. At the same time, a small flow of inert gas enters the center of the funnel insert 74 through the conduit 80 to force the reagent through the open bottom of the insert 74 into the liquid sample. At the same time, a small flow of inert gas is admitted through the bypass conduit 92 into the sample vessel 68 so that the combined pressure of the gas through conduit 92 and conduit 80 will force the gaseous sample through the outlet conduit 96 to the spectrometer cuvette 98. Upon completion of the analysis, the pushbutton 88 of valve 86 is released to restore the reagent vessel 76 to atmospheric pressure and to provide a large purging flow of inert gas through the sample vessel 68.

Figure 3:
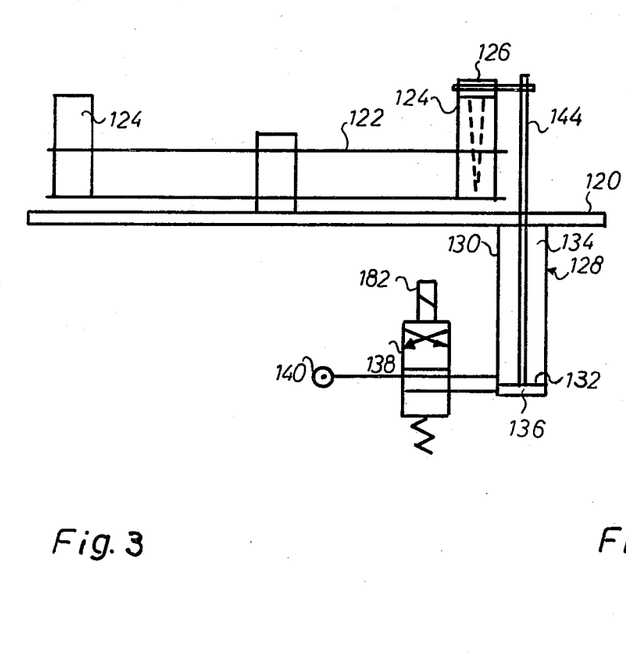
FIG. 3 is a simplified elevation view of a turntable arrangement for automating a series of analyses using the apparatus of the invention.
Figure 4:
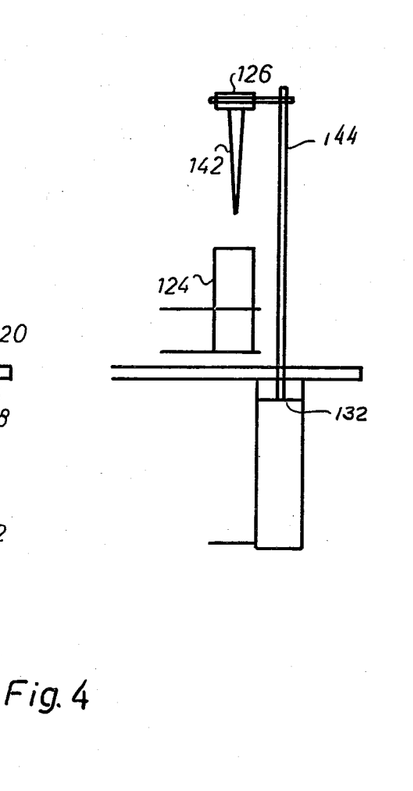
FIG. 4 is a simplified view illustrating a portion of the apparatus of FIG. 3 with the sample vessel closure body lifted.

The apparatus of FIG. 2 may be conveniently applied to automatic analyzing procedures by the use of a turntable arrangement, such as illustrated in the simplified schematic diagram of FIGS. 3 and 4. In FIG. 3, the numeral 120 represents base plate or table that supports a turntable 122 having provisions for carrying an array of sample vessels 124 that are arranged to be advanced stepwise so that each sample vessel is moved consecutively into its operating position as shown on the right side of FIG. 3. When a vessel 124 is advanced into its operative position, a closure body 126 having a sealing plug and funnel-shaped insert 142 is arranged to be placed on top of the sample vessel 124 by means of a piston assembly 128.

The piston assembly 128 comprises a cylinder 130 mounted to and beneath the base plate 120 and containing a double acting piston 132 to which is connected a piston rod 144 that extends through the base plate 120 and to the closure body 126. The piston 132 separates the cylinder 130 into an upper chamber 134 and lower chamber 136, which are both connected through suitable tubing to a directional control valve 138 which may be operated by a solenoid 182 and which is connected to a pneumatic pressure source 140. In the position illustrated in FIG. 3, pressure from the source 140 is directed through the valve 138 into the upper chamber 134 to force the piston 132 and piston rod 144 into its lower position to thereby seal the closure body against the top surface of the sample vessel 124.

As illustrated in FIG. 4, the directional control valve 138 has been reversed to apply pneumatic pressure to the lower chamber 138, whereby the piston 132 and its associated piston rod 144 is raised to the upper position to lift the funnel insert 142 and the closure body 126 from the sample vessel 124.

Figure 5:
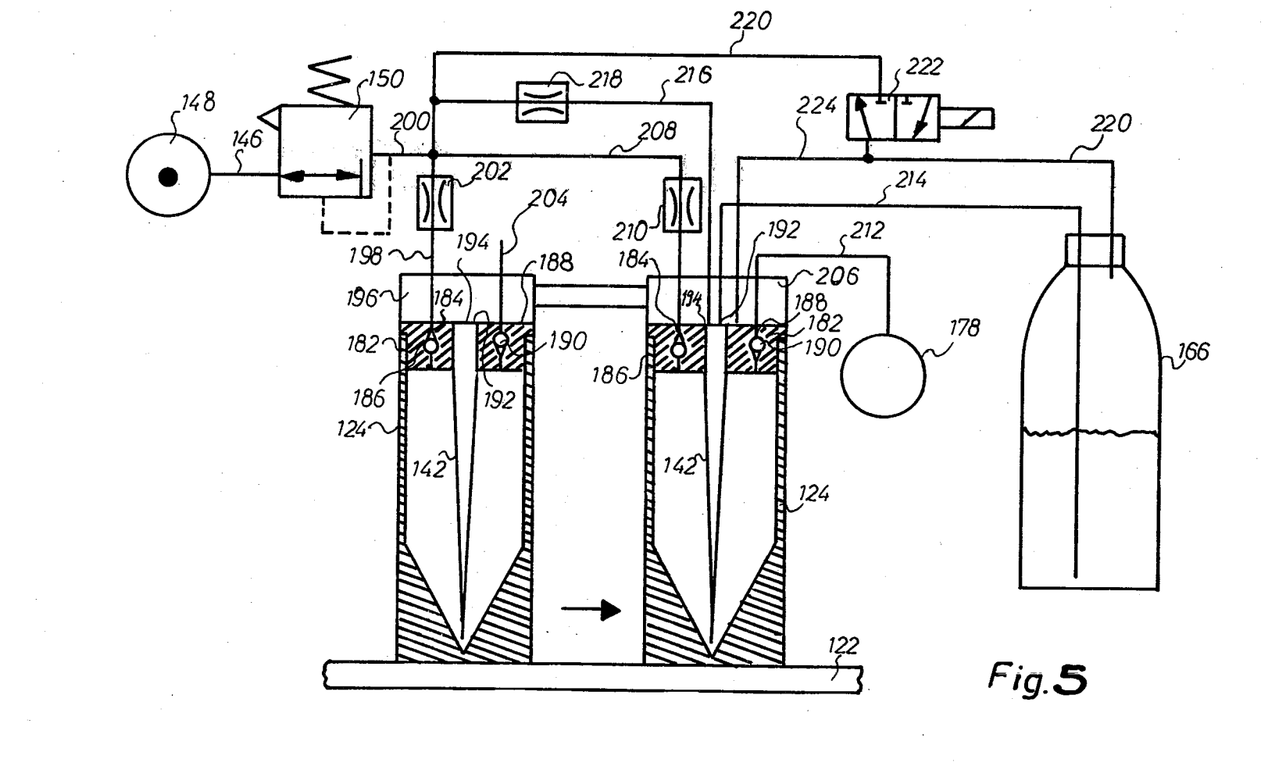
FIG. 5 is a circuit diagram illustrating the details of the apparatus of the invention used with the turntable illustrated in FIGS. 3 and 4.

FIG. 5 is a more detailed diagram illustrating the apparatus of the invention used with a turntable arrangement as described in connection with FIGS. 3 and 4. In the embodiment illustrated in FIG. 5, the turntable 122 is illustrated with two sample vessels in operative positions. The sample vessel 124, mounted at the left in FIG. 5, is in a first operative position where it is being purged of contaminating gases. Thereafter, the table 122 is moved in a direction indicated by the arrow so that the vessel 124 illustrated at the right side on table 122 is in a second operative position where its contents are volatilized and transferred to a spectrometer cuvette for analysis.

Each vessel 124 is closed by a plug 182. Each plug 182 has an inlet 184 and a check valve 186 opening into inlet direction. Each plug 182 also has an outlet 188 with a check valve 190 opening into outlet direction. Each plug 182 supports a funnel-shaped insert 142, as previously described in connection with FIG. 2.

The sample vessels 124 are arranged to be moved consecutively from a first operative position at the left to the second operative position at the right. A first closure body 196 at the first position is connected to a second closure body 206 at the second position. The closure bodies 196 and 206 do not move between the first and second operative positions but are adapted to be lifted by the piston assembly so that each vessel 124 may be moved by the table 122 between the first and second operative positions whereupon the closure bodies 196 and 206 will again be clamped down to secure the plug 182 to the vessel 124. Each of the closure bodies 196 and 206 contain conduits which are connected to the various conduits of the apparatus and which are adapted to coaxially cooperate with the inlets 184, outlets 188, and bores of the funnel inserts 142 in each plug 182.

As shown in FIG. 5, a gas source 148 supplies gas through an inlet tube 146 to a regulator 150, the output of which is connected through tube 200 to a flow restrictor 202 which provides a relatively large gas flow through gas inlet branch 198 and thence through the closure body 196 and inlet 184 into the sample vessel 124 in the first operative position. The inert gas admitted thereto passes through the outlet check valve 190 and gas outlet tubing 204 to the atmosphere and the contents of the sample vessel 124 are thereby flushed of contaminating air and other gases.

The gas outlet tube 200 of regulator 150 also branches to a conduit 216 containing a flow restrictor 218 that admits a small flow of inert gas through the closure 206 into the bore of the funnel-shaped insert 142 of the sample vessel 124 in the second operative position. Gas outlet 200 also communicates an unrestricted flow of inert gas through the conduit 220 into the reagent vessel 166. A solenoid controlled shutoff valve 222 is in the gas conduit 220, as will be subsequently described, and the conduit 220 downstream of the shutoff valve 222 is branched into a vent tube 224 which is directed through the closure 206 where it is sealed against the top surface of the plug 182.

The outlet conduit 200 of the regulator 150 is also applied through a flow restrictor 210 which admits a small flow of inert gas through the closure 206 and inlet 184 into the sample vessel 124 in the second operative position. The outlet of this sample vessel 124 is through the check valve 190 in the closure plug 182 and through outlet 188 into the outlet conduit 212 which is directed to the atomic cuvette 178 of the associated absorption spectrometer.

In operation, the sample vessel 124 in the first operation position, illustrated at the left of the drawing of FIG. 5, is continually flushed by the admission of inert gas through flow restrictor 202 in gas inlet branch 198, the gas and impurities then emerging from the sample vessel 124 through check valve 190 and exhaust tube 204. While the vessel in the first operating position is being flushed, the sample vessel 124 in the second operating position to the right is ready to be sampled for spectrometer analyses. The inert gas shutoff valve 222 is first energized so that gas from the regulator 150 will be applied through the conduit 220 into the reagent vessel 166. The applied gas pressure within the vessel 166 thereby forces the reagent through the reagent conduit 214 into the center of the funnel insert 142 of the sample vessel 124 in the right or second operative position. A small flow of inert gas through the flow restrictor 218 and the conduit 216 forces the sample within the insert 142 from the open end and into the bottom conical portion of the sample vessel 124 as previously described. Simultaneously, a small flow of inert gas is applied through the inlet branch 208 and the restrictor 210 into the inlet 184 and check valve 186 into the interior of the sample vessel so that the gaseous sample produced by the admission of the reagent, passes through the check valve 190 and into the outlet tubing 212 to the cuvette 178.

When the measurement has been completed, the shutoff valve 222 is returned to its inoperative position, as shown, to shut off the gas flow into the reagent vessel 166. At this point, the closure bodies 196 and 206 are lifted from the top of the sample vessels 124 so that the table 122 may advance the vessel from the first operating position to the second operating position. When closure 206 is lifted from the plug 182, the end of the vent tube 224, which previously was sealed against the top surface of the plug 182, is now opened to atmospheric pressure, thereby releasing the pressure within the reagent vessel 166 and preventing any siphoning of the reagent into the funnel insert 142.

With the arrangement described, the analysis time of various samples can be greatly shortened since the process of flushing the sample vessel in a first operating position and dispensing the reagent and transferring the volatile substances from the sample vessel in the second operating position is effected simultaneously. Furthermore, in the embodiment described in FIG. 5, all sample vessels are effectively sealed against accidental contamination by the check valves within their respective plugs.

What is claimed is:

1. Apparatus for generating a gaseous test sample from a liquid sample and for transferring the test sample to a measuring cuvette of an atomic absorption spectrometer, comprising:

a sample vessel, a closure plug for closing said sample vessel, means defining a source for supplying inert gas under pressure, means for adding a reagent to said sample vessel including a sealed reagent supply vessel, a reagent dispensing conduit having a first end located in said reagent supply vessel for withdrawing reagent from said reagent supply vessel and a second end terminating adjacent said plug in said sample supply vessel above the level of sample in the sample supply vessel, conduit means including a valve interconnecting the source of inert gas and said reagent supply vessel for supplying inert gas under pressure to said reagent supply vessel and displacing reagent from said reagent supply vessel through said dispensing conduit into said sample vessel, and a reagent flow conduit carried by said plug and disposed within said sample supply vessel in communication with said second end of said reagent dispensing conduit, said reagent flow conduit having an end terminating in an aperture adjacent the bottom of said sample vessel and below the level of sample therein whereby reagent may be transmitted from said second end along said flow conduit and outwardly through said aperture for bubbling upwardly within the sample supply vessel, a gas inlet passage coupling said source of inert gas through said plug and the bore of said reagent flow conduit into said sample vessel, and a gaseous sample outlet conduit connected to said closure plug for transferring test sample under pressure from said sample vessel to the measuring cuvette.

2. Apparatus according to claim 1 wherein said reagent flow conduit provides a gap between said second end and the end of said flow conduit adjacent the bottom of the sample vessel to preclude reverse syphoning of sample from said sample vessel to said reagent vessel.

3. The apparatus according to claim 1 wherein said reagent flow conduit includes a generally conically shaped insert carried by said plug, said reagent dispensing conduit terminating in said second end thereof in communication with the bore of said insert, said insert being disposed within the sample supply vessel and having said aperture located adjacent its lower end and the bottom of said sample supply vessel below the level of sample therein for communicating the contents of said insert to said sample vessel.

4. The apparatus according to claim 1 including means for restricting the flow of inert gas into said sample supply vessel through said gas inlet passage.

5. The apparatus according to claim 4 including a second inert gas inlet passage coupling said inert gas source means through said plug into said sample vessel, said second inert gas inlet passage being sized to admit a large flow of inert gas from said inert gas source means into the sample supply vessel in comparison with the flow of inert gas through the first gas inlet passage, said valve being movable between first and second positions, said valve in said first position enabling large flow of inert gas through said second inlet passage for flushing said sample vessel and opening said reagent supply vessel to atmosphere through said conduit means, said valve in said second position blocking inert gas flow through said second inlet passage and supplying inert gas through said conduit means to said reagents supply vessel and displacing reagent therefrom through said dispensing conduit into said sample vessel.

6. Apparatus for generating a gaseous test sample from a liquid sample and for transferring the test sample to a measuring cuvette of an atomic absorption spectrometer, comprising:

a plurality of sample vessels, a closure plug for closing each said sample vessel, means defining a source for supplying inert gas under pressure, conveying means for supporting a plurality of sample supply vessels and for advancing said vessels into first and second operating positions, said conveying means including non-advancing first and second closure bodies adapted to be successively placed in close contact with the top surface of each said sample vessel closure plug in said first and second operating positions respectively, said first and second closure bodies containing a plurality of conduits cooperatively coupled to corresponding conduits in said closure plug, means for adding a reagent to said sample vessel including a sealed reagent supply vessel, a reagent dispensing conduit having a first end located in said reagent supply vessel for withdrawing reagent from said reagent supply vessel and a second end terminating in said second closure body adjacent said plug in said sample supply vessel and above the level of sample therein when said sample supply vessel lies in its second position, conduit means including a valve for interconnecting the source of inert gas and said reagent supply vessel for supplying inert gas under pressure to said reagent supply vessel and displacing reagent from said reagent supply vessel through said dispensing conduit into said sample vessel when in said second position, and a reagent flow conduit carried by said plug and disposed within said sample supply vessel in communication with said second end of said reagent dispensing conduit, when said sample vessel lies in its second position, said reagent flow conduit having an end terminating in an aperture adjacent the bottom of said sample vessel and below the level of sample therein whereby reagent may be transmitted from said second end along said flow conduit and outwardly through said aperture for bubbling upward within the sample supply vessel, a gas inlet passage coupling said source of inert gas through said plug and the bore of said reagent flow conduit into said sample vessel, and an outlet conduit connected to said closure plug enabling egress of gas from said sample vessel.

7. The apparatus set forth in claim 6 wherein said first closure body in said first position is coupled to said source of inert gas and includes flow restricting means for supplying a relatively large flow of said gas through said closure body and said gas inlet passage into said sample vessel in said first position of said sample vessel, said first closure body further including a second conduit aligned with said outlet conduit in said closure plug of said sample vessel for venting said sample vessel to the atmosphere when said sample vessel lies in its first operating position.

8. The apparatus set forth in claim 6 wherein the intake and venting conduits in said closure plug include check valves for preventing contamination of the contents of said sample vessel in the absence of inert gas pressure.

9. The apparatus as set forth in claim 8 wherein the second closure body positioned on the closure plug of the sample supply vessel in the second operating position includes a first conduit cooperating with the gas inlet passage of said closure plug for admitting a relatively small flow of inert gas into said sample supply vessel, a second conduit cooperating with the outlet conduit of said closure plug for communicationg the contents of said sample supply vessel to the spectrometer cuvette, a third conduit aligned with the bore of said reagent flow conduit for admitting a relatively small flow of inert gas therein a fourth conduit aligned with the bore of said reagent flow conduit for admitting reagent from said reagent vessel, and a fifth conduit to said closure body and terminating on the top surface of said closure plug, said fifth conduit communicating with the gas inlet conduit to said reagent supply vessel.

10. The apparatus as set forth in claim 9 further including a conduit means including a shutoff valve between said source of inert gas and said reagent vessel for displacing the contents of said reagent vessel through said fourth closure body conduit into said reagent flow conduit in said sample supply vessel, said inlet conduit being maintained at the pressure of said inert gas until said second sample supply vessel closure body is removed whereby said closure body fifth conduit is opened to admit atmospheric pressure to said reagent vessel.

* * * * *

UNITED STATES PATENT AND TRADEMARK OFFICE
CERTIFICATE OF CORRECTION

PATENT NO. :  4,208,372
DATED      :  June 17, 1980
INVENTOR(S) :  Bernhard Huber It is certified that error appears in the above-identified patent and that said Letters Patent are hereby corrected as shown below:

Column 2, line 47, change "atomosphere" to --atmosphere--.

Column 9, line 13, change "communicationg" to --communicating--.

Column 10, line 11, before "sample", insert --second--.

Signed and Sealed this

Tenth Day of March 1981

[SEAL]

Attest:

RENE D. TEGTMEYER

*Attesting Officer*  *Acting Commissioner of Patents and Trademarks*